(12) United States Patent
Iannotti et al.

(10) Patent No.: US 9,254,155 B2
(45) Date of Patent: Feb. 9, 2016

(54) SYSTEM AND METHOD FOR ASSISTING WITH ARRANGEMENT OF A STOCK INSTRUMENT WITH RESPECT TO A PATIENT TISSUE

(75) Inventors: Joseph P. Iannotti, Strongsville, OH (US); Wael K. Barsoum, Bay Village, OH (US); Jason A. Bryan, Avon Lake, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 0 days.

(21) Appl. No.: 13/282,528

(22) Filed: Oct. 27, 2011

(65) Prior Publication Data
US 2012/0109226 A1  May 3, 2012

Related U.S. Application Data

(60) Provisional application No. 61/408,376, filed on Oct. 29, 2010.

(51) Int. Cl.
| | |
|---|---|
| *A61B 17/56* | (2006.01) |
| *A61B 17/88* | (2006.01) |
| *A61B 19/00* | (2006.01) |
| *A61B 17/17* | (2006.01) |

(52) U.S. Cl.
CPC ................ *A61B 17/88* (2013.01); *A61B 19/50* (2013.01); *A61B 2017/1778* (2013.01); *A61B 2019/508* (2013.01)

(58) Field of Classification Search
CPC ....................................................... A61B 19/50
USPC ................................ 606/81, 86 R, 87–89, 91
See application file for complete search history.

(56) References Cited

U.S. PATENT DOCUMENTS

2003/0100906 A1* 5/2003 Rosa et al. ........................ 606/86
2004/0133276 A1* 7/2004 Lang et al. .................... 623/14.12

(Continued)

FOREIGN PATENT DOCUMENTS

EP    1 639 949 A1    3/2006

OTHER PUBLICATIONS

Barsoum U.S. Appl. No. 13/178,324, filed Jul. 7, 2011, entitled "Method and Apparatus for Providing a Relative Location Indication During a Surgical Procedure".

(Continued)

*Primary Examiner* — Samuel Hanna
(74) *Attorney, Agent, or Firm* — Norton Rose Fulbright Canada LLP

(57) ABSTRACT

A stock instrument includes at least one guide interacting feature. A lower instrument surface of the stock instrument is placed into contact with the patient tissue. A guide has a lower guide surface contoured to substantially mate with at least a portion of an upper instrument surface of the stock instrument. A predetermined instrument orientation upon the patient tissue is defined, which is preselected responsive to preoperative imaging of the patient tissue. The guide and instrument are mated in a predetermined relative guide/instrument orientation wherein at least one guide interacting feature of the instrument is placed into engagement with at least one instrument guiding feature of the guide. The guide is moved into a predetermined guide orientation with respect to the patient tissue and concurrently the instrument is moved into a predetermined instrument orientation with respect to the patient tissue.

17 Claims, 9 Drawing Sheets

(56) References Cited

U.S. PATENT DOCUMENTS

| | | | |
|---|---|---|---|
| 2005/0234461 A1* | 10/2005 | Burdulis et al. | 606/79 |
| 2006/0074430 A1 | 4/2006 | Deffenbaugh et al. | |
| 2007/0270973 A1* | 11/2007 | Johnson | A61F 2/4609 623/17.16 |
| 2008/0195109 A1* | 8/2008 | Hunter et al. | 606/87 |
| 2008/0269906 A1 | 10/2008 | Iannotti et al. | |
| 2008/0287954 A1 | 11/2008 | Kunz et al. | |
| 2008/0312659 A1* | 12/2008 | Metzger et al. | 606/87 |
| 2009/0018546 A1 | 1/2009 | Daley | |
| 2009/0024131 A1* | 1/2009 | Metzger et al. | 606/88 |
| 2009/0088754 A1* | 4/2009 | Aker et al. | 606/79 |
| 2009/0088763 A1* | 4/2009 | Aram et al. | 606/88 |
| 2010/0152782 A1 | 6/2010 | Stone et al. | |
| 2010/0217338 A1* | 8/2010 | Carroll et al. | 606/86 R |
| 2011/0190775 A1 | 8/2011 | Ure | |
| 2012/0245647 A1 | 9/2012 | Kunz et al. | |

OTHER PUBLICATIONS

Iannotti et al., U.S. Appl. No. 61/408,324, filed Oct. 29, 2010, entitled "System and Method for Assisting with Attachment of a Stock Implant to a Patient Issue".

Iannotti et al., U.S. Appl. No. 61/408,359, filed Oct. 29, 2010, entitled "System and Method for Association of a Guiding Aid with a Patient Tissue".

Iannotti et al., U.S. Appl. No. 61/408,392, filed Oct. 29, 2010, entitled "System of Preoperative Planning and Provision of Patient-Specific Surgical Aids".

* cited by examiner

SYSTEM AND METHOD FOR ASSISTING WITH ARRANGEMENT OF A STOCK INSTRUMENT WITH RESPECT TO A PATIENT TISSUE

RELATED APPLICATION

This application claims priority from U.S. Provisional Application No. 61/408,376, filed Oct. 29, 2010, the subject matter of which is incorporated herein by reference in its entirety.

TECHNICAL FIELD

The present invention relates to a system and method for use of a surgical guide and, more particularly, to a system and method for use of a surgical guide for assisting with arrangement of a stock instrument with respect to a patient tissue.

BACKGROUND OF THE INVENTION

The efficient functioning of the shoulder joints is important to the well-being and mobility of the human body. Each shoulder joint includes the upper portion of the humerus, which terminates in an offset bony neck surmounted by a ball-headed portion known as the humeral head. The humeral head rotates within a socket, known as the glenoid fossa, in the scapula to complete the shoulder joint. Diseases such as rheumatoid- and osteo-arthritis can cause erosion of the cartilage lining of the glenoid fossa so that the ball of the humerus and the scapula rub together, causing pain and further erosion. Bone erosion may cause the bones themselves to attempt to compensate for the erosion which may result in the bone becoming deformed. This misshapen joint may cause pain and may eventually cease to function altogether.

Operations to replace the shoulder joint with an artificial implant are well-known and widely practiced. Generally, the shoulder prosthesis will be formed of two components, namely: a glenoid, or socket, component which lines the glenoid fossa, and a humeral, or stem, component which includes a weight-bearing ball and replaces the humeral head. (Each of these components may be made up of multiple subassemblies.) Alternately, a reverse shoulder prosthesis has a ball as the glenoid component and a socket as the humeral component, but the following description presumes a standard, not reverse, shoulder prosthesis arrangement. During the surgical procedure for implanting the shoulder prosthesis, the remaining cartilage or damaged tissue is removed from the glenoid fossa using a reamer such that the native glenoid fossa will accommodate the outer surface of the glenoid component of the shoulder prosthesis. The glenoid component of the prosthesis can then be inserted into the prepared glenoid fossa. Generally, fixing means such as screws and/or bone cement may be used to hold the glenoid component in the glenoid fossa. There is also generally an implant stem provided to the glenoid implant, the stem being inserted into a prepared cavity in the glenoid fossa to anchor the glenoid implant. The use of additional fixing means and anchor(s) helps to provide stability after the prosthesis has been inserted. In some modern prosthesis, the glenoid component may be coated on its external surface with a bone growth promoting substance which will encourage bone ingrowth which also helps to hold the glenoid component in place. The humeral head also is removed during the surgical procedure, and the humerus shaft hollowed out using reamers and rasps to accept the humeral component of the prosthesis. The stem portion of the prosthesis is inserted into the humerus and secured therein to complete the shoulder joint replacement.

In order to strive toward desired performance of the combined glenoid and humeral shoulder prosthesis components, the glenoid portion should be properly positioned upon the glenoid fossa (among other considerations). The glenoid portion positioning is particularly important since incorrect positioning of the glenoid component can lead to the prosthetic shoulder joint suffering from dislocations, a decreased range of motion, and possibly eventual loosening and/or failure of one or both components of the joint.

Generally, the normal glenoid retroversion of a given patient may fall within a range of approximately 20° (5° of anteversion and 15° of retroversion). (The version of the glenoid is defined as the angle between the plane of the glenoid fossa to the plane of the scapula body.) In the pathologic state, glenoid bone loss may result in a much larger range of version angles.

One goal of shoulder surgery may be to modify the pathologic bone to correct pathologic version to be within the normal range or the normal version of the patient's native anatomy before the bone loss occurred. During surgery, and particularly minimally invasive procedures, the plane of the scapula may be difficult or impossible to determine by direct visual inspection, resulting in the need for assistive devices or methods to define both the pathologic version present at the time of surgery and the intended correction angle.

It is generally believed that there is a preferred orientation for the glenoid component to provide a full range of motion and to minimize the risk of dislocation or other mechanical component failure. Some example orientations of the glenoid prosthesis relative to the glenoid face are about 5° of anteversion to about 15° of retroversion; average version is about 1-2° of retroversion. This broadly replicates the natural angle of the glenoid. However, the specific angular orientation of the glenoid portion varies from patient to patient.

With a view to overcoming these disadvantages, some arrangements have been recently suggested in which a three-dimensional intraoperative computer imaging surgical navigation system is used to render a model of the patient's bone structure. This model is displayed on a computer screen and the user is provided with intraoperative three-dimensional information as to the desired positioning of the instruments and the glenoid component (or any component, depending on the subject patient tissue) of the prosthetic implant. However, surgical navigation arrangements of this type are not wholly satisfactory since they generally use only a low number of measured landmark points to register the patient's anatomy and to specify the angle of the prosthetic implant component (e.g., a glenoid component), which may not provide the desired level of accuracy. Further, the information provided by such systems may be difficult to interpret and may even provide the user with a false sense of security. Moreover, these systems are generally expensive to install and operate and also have high user training costs. Various proposals for trial prosthetic joint components and assistive instruments have been made in an attempt to overcome the problems associated with accurately locating the glenoid portion of the prosthetic implant. While these trial systems and instruments may help with checking whether the selected position is correct, they are not well-suited to specify the correct position initially, and thus there still is user desire for a system which may assist a user in placement of prosthetic implant component in a prepared native tissue site.

SUMMARY OF THE INVENTION

In an embodiment of the present invention, a method of arranging a stock instrument with respect to a patient tissue is described. The stock instrument includes at least one guide interacting feature. A lower instrument surface of the stock instrument is placed into contact with the patient tissue. A guide having a lower guide surface contoured to substantially mate with at least a portion of an upper instrument surface of the stock instrument, an upper guide surface spaced longitudinally apart from the lower guide surface by a guide body, and at least one instrument guiding feature at a predetermined feature location with respect to the guide body is provided. A predetermined instrument orientation upon the patient tissue is defined. The predetermined instrument orientation is preselected responsive to preoperative imaging of the patient tissue. The lower guide surface is placed into mating contact with at least a portion of the upper instrument surface in a predetermined relative guide/instrument orientation wherein at least one guide interacting feature of the instrument is placed into engagement with at least one instrument guiding feature of the guide. The guide is moved into a predetermined guide orientation with respect to the patient tissue and concurrently the instrument is moved into a predetermined instrument orientation with respect to the patient tissue.

In an embodiment of the present invention, a guide for assisting with arrangement of a stock instrument with respect to a patient tissue is described. A lower guide surface is configured to contact an upper instrument surface of the stock instrument when a lower instrument surface of the stock instrument is in contact with the patient tissue. The lower guide surface is contoured to substantially mate with at least a portion of the upper instrument surface. An upper guide surface is spaced longitudinally apart from the lower guide surface by a guide body. The upper guide surface is accessible to a user when the lower guide surface is in contact with the upper instrument surface. An orienting feature is configured to enter a predetermined orienting relationship with a previously placed landmark while the lower guide surface is in mating contact with at least a portion of the upper instrument surface in a predetermined relative guide/instrument orientation. The predetermined orienting relationship indicates that the instrument has achieved a predetermined instrument relationship with the patient tissue.

BRIEF DESCRIPTION OF THE DRAWINGS

For a better understanding of the invention, reference may be made to the accompanying drawings, in which.

DESCRIPTION OF EMBODIMENTS

Figure 1:
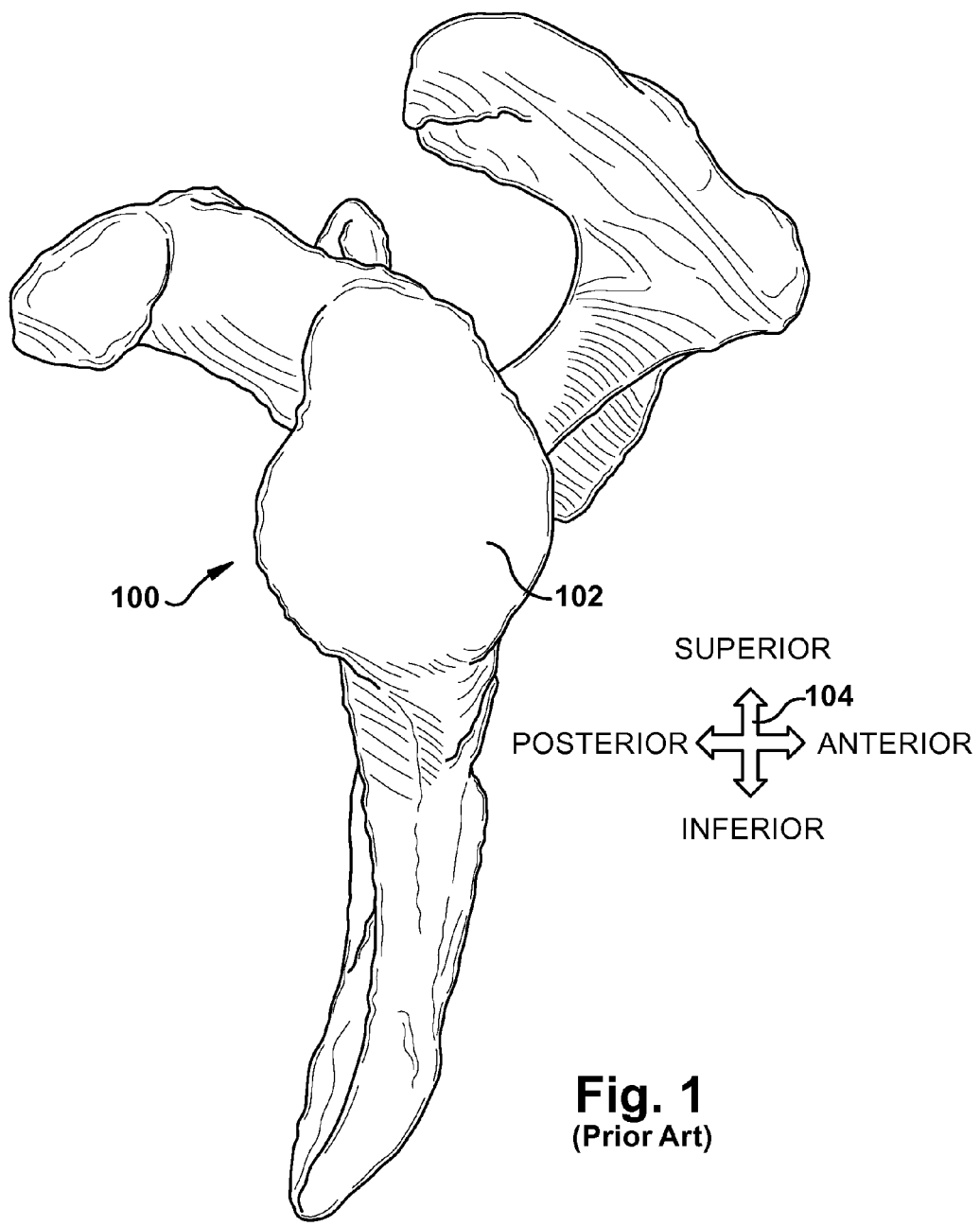
FIG. 1 is a perspective top view of an example use environment.
Figure 2:
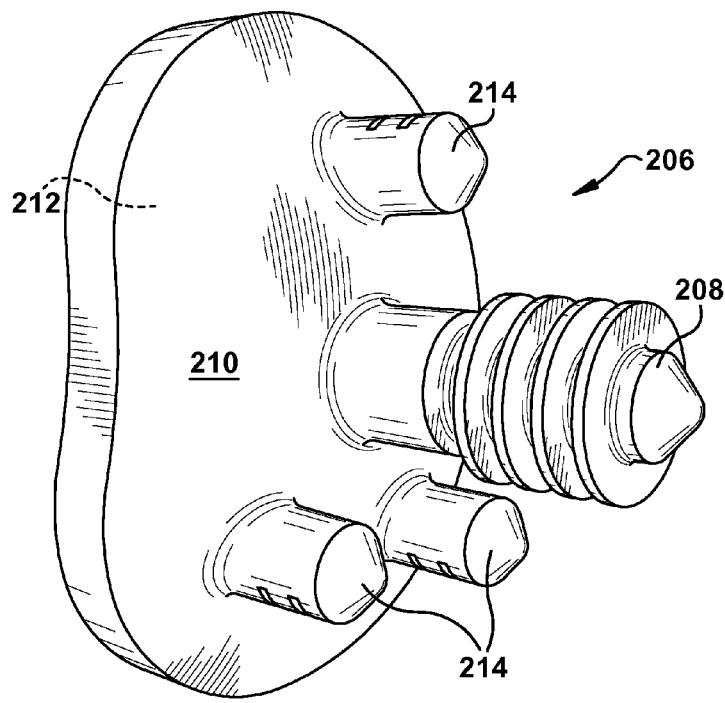
FIG. 2 is a perspective bottom view of a first prior art prosthetic component.

FIG. 1 depicts a portion of the external surface of a (left) scapula 100, which is an example of a possible patient tissue use environment for the described systems, apparatuses, and methods, with particular emphasis on the glenoid fossa 102. Directional arrow 104 indicates the superior/inferior and anterior/posterior directions. A glenoid implant 206, shown in FIG. 2, is the stock prosthetic implant for use with a prosthetic shoulder replacement surgery for the described embodiments of the present invention. The glenoid implant 206 includes an implant shaft 208, a lower implant surface 210, an upper implant surface 212 (hidden in this view, as shown via dashed line), and a plurality of fastening pegs 214 extending from the lower implant surface. The patient tissue is shown and described herein at least as a scapula and the prosthetic implant component is shown and described herein at least as an glenoid prosthetic shoulder component, but the patient tissue and corresponding prosthetic implant component could be any desired types such as, but not limited to, hip joints, shoulder joints, knee joints, ankle joints, phalangeal joints, metatarsal joints, spinal structures, long bones (e.g., fracture sites), or any other suitable patient tissue use environment for the present invention. For example, the prosthetic implant component could be an internal fixation device (e.g., a bone plate), a structure of a replacement/prosthetic joint, or any other suitable artificial device to replace or augment a missing or impaired part of the body.

The term "lateral" is used herein to refer to a direction indicated by directional arrow 104 in FIG. 1; the lateral direction in FIG. 1 lies substantially within the plane of the drawing and includes all of the superior, inferior, anterior, and posterior directions. The term "longitudinal" is used herein to refer to a direction defined perpendicular to the plane created by directional arrow 104, with the longitudinal direction being substantially into and out of the plane of the drawing in FIG. 1 and representing the proximal (toward the medial line of the body) and distal (out from the body) directions, respectively.

Figure 3:
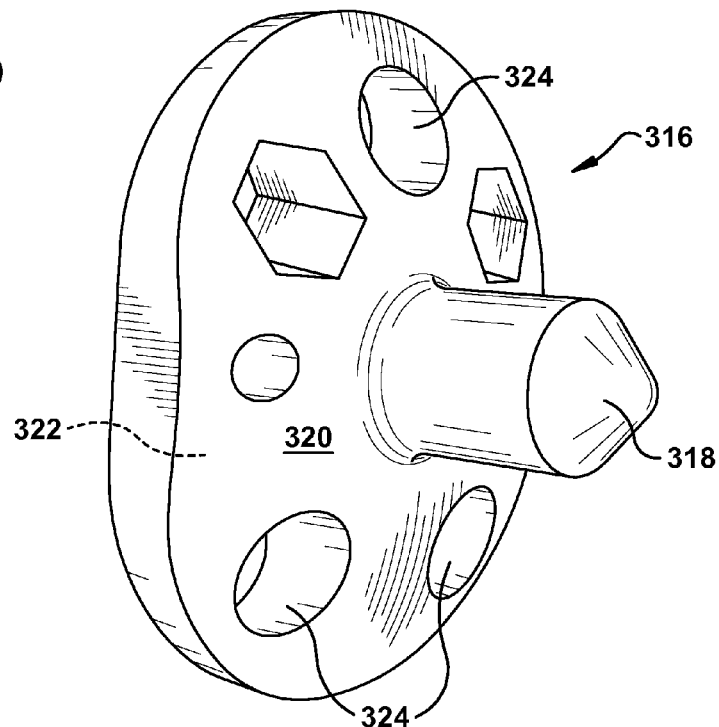
FIG. 3 is a perspective bottom view of a first prior art instrument for use with the component of FIG. 2.

During installation of the glenoid implant 206, a shaft aperture (not shown) is drilled into the patient tissue (here, the patient's glenoid fossa 102) at a predetermined location and a stock instrument is used to help prepare the patient tissue surface. The stock instrument is depicted here as a glenoid instrument 316 according to a first embodiment of the present invention, shown in FIG. 3. Suitable instruments 316 similar to those shown herein are available from DePuy Orthopaedics, Inc., of Warsaw, Ind. The instrument 316 includes an instrument shaft 318, a lower instrument surface 320, an upper instrument surface 322 (hidden in this view, as shown via dashed line), and at least one guide interacting feature 324.

The term "stock" is used herein to indicate that the component indicated is not custom-manufactured or -configured for the patient, but is instead provided as a standard inventory item by a manufacturer. A particular stock component may be selected by the user from a product line range of available components, with the user specifying a desired configuration, general or particular size (e.g., small, medium, large or a specific measurement), material, or any other characteristic of the component. Indeed, the stock component could be manufactured only after the user has selected the desired options from the range of choices available. However, the stock component is differentiated from a custom-manufactured or bespoke component in that the stock component is agnostic and indifferent regarding a particular patient anatomy during the design and manufacturing processes for an implant intended for that patient, while the patient anatomy is an input into at least one design and/or manufacturing process for a custom-manufactured component. The following description presumes the use of a stock instrument, though one of ordinary skill in the art will be able to provide for the use of the present invention with a custom-manufactured instrument, instead.

At least one of the guide interacting features 324 may bear a direct positional relationship to some feature of the glenoid implant 206. Here, the guide interacting features 324 are located analogously to the fastening pegs 214 of the glenoid implant 206 and may later assist in guiding some aspect of patient tissue modification to ready the glenoid fossa 102 for the glenoid implant 206 in a known manner and as will be discussed in further detail below.

Figure 4:
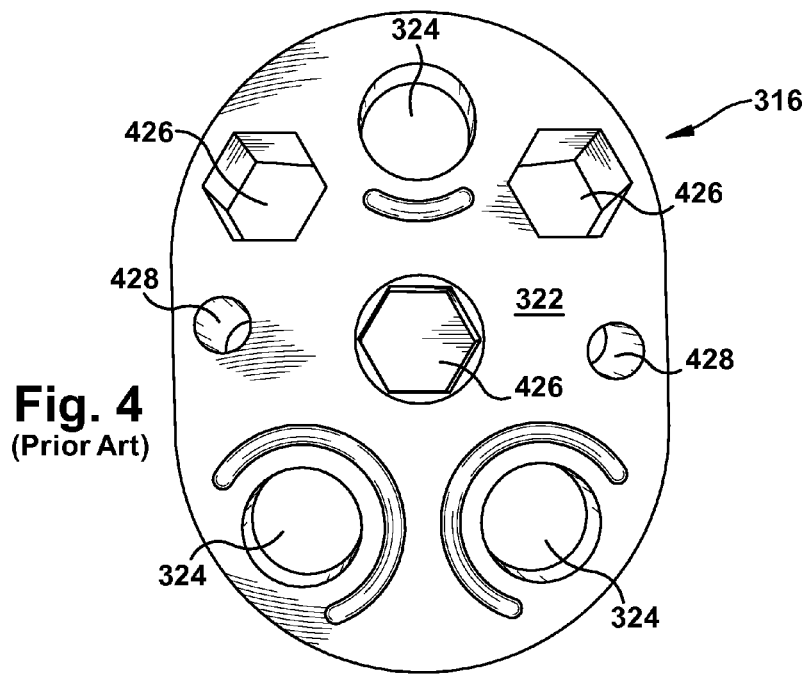
FIG. 4 is a top view of the instrument of FIG. 3.

As can be seen in FIG. 4, the instrument 316 according to the first embodiment of the present invention may include at least one handling feature 426 to accept a handle (not shown) which the user may manipulate to move the instrument at or near the surgical site—two throughhole handling features and one closed (blind) cavity handling feature are shown in the Figures. The instrument 316 may also include one or more securing features 428 for assisting with holding the instrument 316 in a predetermined instrument with the patient tissue, if desired.

During installation of the glenoid implant 206, it is known for a user to place a stock instrument 316 on the patient tissue to help guide surgical tools used to prepare the patient tissue to receive the glenoid implant. For example, a central shaft aperture (which will later receive the implant shaft 218) can be machined at a desired location on the glenoid fossa 102, and the instrument shaft 318 can be placed into the shaft aperture to help hold the instrument 316 in place while the instrument is used as a template for the user to drill, ream, cut, scrape, graft, or otherwise modify the patient tissue from a native or pathologic state to accept the glenoid implant 206 as desired according to the preoperative plan and/or an intraoperative decision.

The shaft aperture can be located on the glenoid fossa 102 by the user with relatively little difficulty, such as with the assistance of a landmark (not shown), such as a guide pin, wire, marking, and/or other location indicator previously placed in a predetermined relationship with the patient tissue. The landmark may be any suitable two- or three-dimensional landmark such as, but not limited to, a native or acquired anatomical feature of the patient tissue and/or a separately provided landmark placed with the assistance of a guide as disclosed in co-pending U.S. patent application Ser. No. 13/282,509, filed Oct. 27, 2011, titled "System and Method for Association of a Guiding Aid with a Patient Tissue" and claiming priority to U.S. Provisional Patent Application No. 61/408,359, filed Oct. 29, 2010 and titled "System and Method for Association of a Guiding Aid with a Patient Tissue", the entire contents of both of which are incorporated herein by reference. The landmark could also or instead be placed using a robotic surgical aid, adjustable reusable (e.g., "dial-in") tools, intraoperative imaging, or any other suitable placement aid. Optionally, an original landmark could have been previously placed, then removed for any reason (e.g., to facilitate machining of the glenoid fossa 102 surface). A second landmark may then be placed at the same location and with the same location as the original landmark, such as via reusing the cavity in the surface left by the removal of the original landmark. Indeed, the remaining cavity in the surface itself may serve a landmarking function, Through these or any other such transformations of physical manifestations, the position information represented by the original landmark and preoperatively planned may be preserved and used during various stages of the surgical procedure regardless of the way in which that position landmark is made available to the user at those various stages.

Once the shaft aperture is located as desired and the instrument shaft 318 is inserted to substantially place the lower instrument surface 320 in contact with the patient tissue of the glenoid fossa 102, however, the instrument 316 may still be in an orientation that does not comport with a preoperatively planned positioning. Once the instrument shaft 318 is located inside the shaft aperture, the instrument 316 can pivot about an axis provided by the instrument shaft. For precision in pivoting the instrument into a desired rotational orientation with respect to the glenoid fossa 102, the user may choose to employ a guide 530, such as that shown in FIGS. 5-7.

Figure 5:
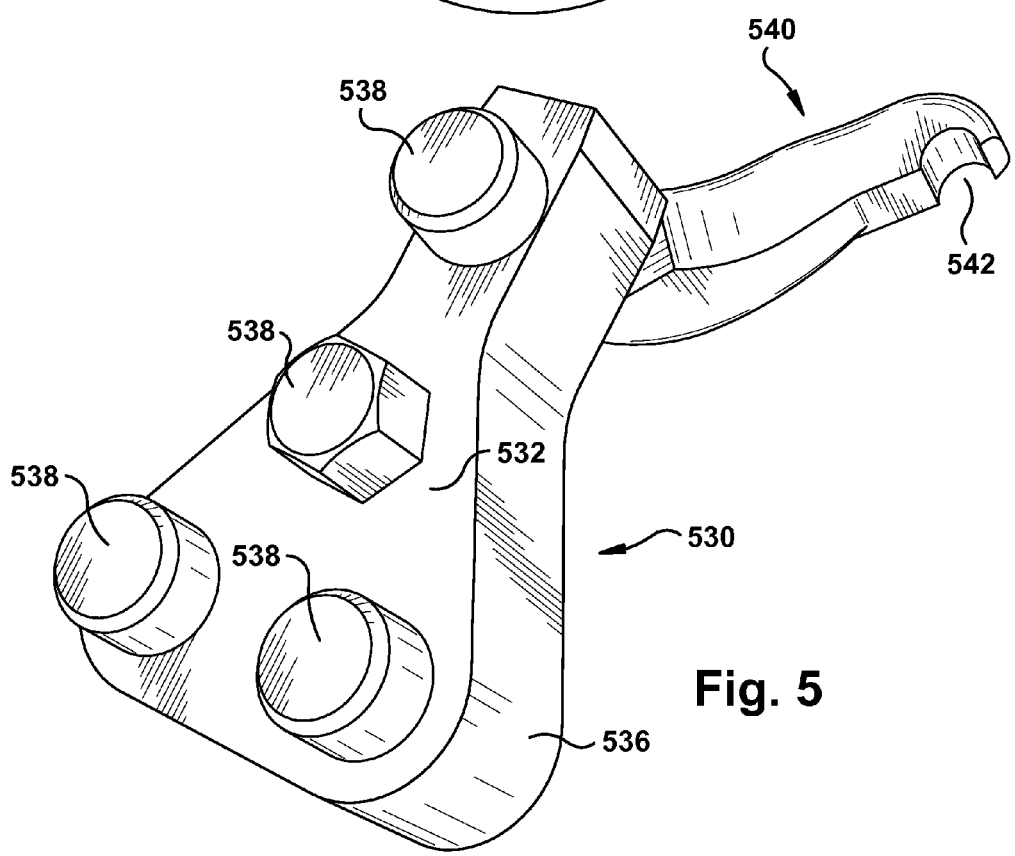
FIG. 5 is a perspective bottom view of an embodiment of the present invention.
Figure 6:
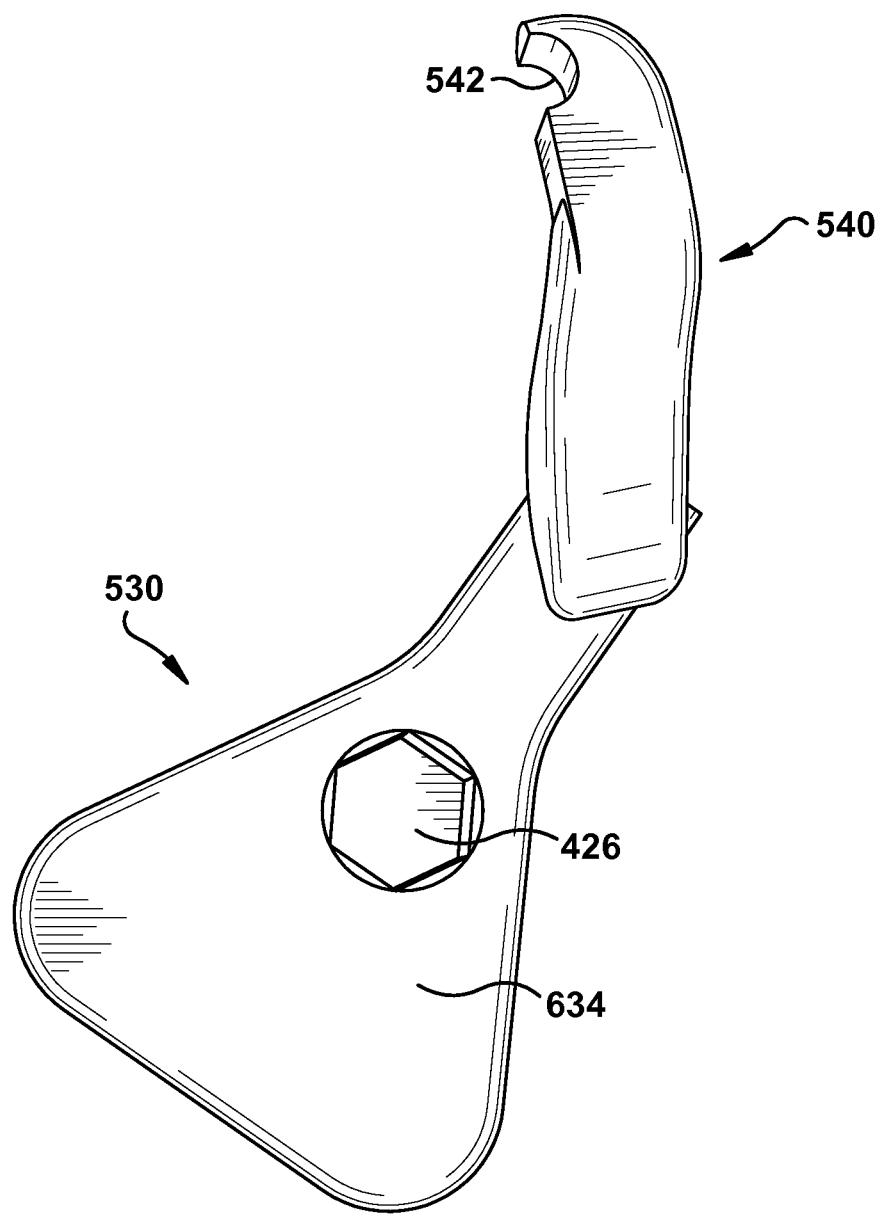
FIG. 6 is a top view of the embodiment of FIG. 5.

With reference to FIGS. 5-6, a guide 530 has a lower guide surface 532 configured to contact an upper instrument surface 322 of the instrument 316 when a lower instrument surface 320 of the instrument is in contact with the glenoid fossa 102. The lower guide surface 532 is contoured to substantially mate with at least a portion of the upper instrument surface 322, as will be discussed below. The term "mate" is used herein to indicate a relationship in which the contours of two structures are at least partially matched or coordinated in at least two dimensions. For example, both the lower guide surface 532 and the upper instrument surface 322 could have profiles that are concavely curved, convexly curved, planar/linear, or any combination of those or other profile shapes. The guide 530 also includes an upper guide surface 634 spaced longitudinally apart from the lower guide surface 532 by a guide body 536. The upper guide surface 634 is accessible to a user when the lower guide surface 532 is in contact with the upper instrument surface 322.

The patient's name, identification number, surgeon's name, and/or any other desired identifier may be molded into, printed on, attached to, or otherwise associated with the guide 530 in a legible manner. The guide 530 may be made by any suitable method such as, but not limited to, selective laser sintering ("SLS"), fused deposition modeling ("FDM"), stereolithography ("SLA"), laminated object manufacturing ("LOM"), electron beam melting ("EBM"), 3-dimensional printing ("3DP"), contour milling from a suitable material, computer numeric control ("CNC"), other rapid prototyping methods, or any other desired manufacturing process.

The guide 530 may include at least one instrument guiding feature 538 at a predetermined feature location with respect to the guide body 536. At least one guide interacting feature 324 of the instrument 316 may be configured for engagement with at least one instrument guiding feature 538 of the guide 530. As shown in FIG. 5, each instrument guiding feature 538 is a protrusion from the lower guide surface 532 and each guide interaction feature 324 is a cavity, and the protrusion enters the cavity to engage the guide 530 and the instrument 316 in the mating contact in the predetermined relative guide/instrument orientation. However, one of ordinary skill in the art could readily reverse that cavity/protrusion status for one or more guide interacting features 324 and/or instrument guiding features 538, or could provide different mechanical structures (i.e., other than a cavity or protrusion) to carry out the described engagement.

As can be seen in FIG. 5, the lower guide surface 532 includes a hexagon-shaped protruding instrument guiding feature 538, which may be configured to engage with a correspondingly located and complementarily shaped handling feature 426 of the instrument 316 to supplement or supplant the engagement of the round instrument guiding features in transferring motive force between the guide 530 and the instrument 316. It is contemplated that engagement between one or more guide interacting features 324 and instrument guiding features 538 will assist the user with concurrently moving one of the guide 530 and the instrument 316 via a motive force exerted on the other of the guide and the instrument. Alternately, the user may directly grasp and move both the guide 530 and the instrument 316 at once—in this situation, the engagement between the guide interacting features 324 and instrument guiding features 538 may simply assist with maintaining the guide and the instrument in the predetermined relative guide/instrument orientation. Here, the hexagonal instrument guiding feature 538 is collinear with the handling feature 426, which is collinear with the instrument shaft 318. Because the instrument shaft 318 may interact with a shaft aperture in the patient tissue serving as a landmark, the hexagonal instrument guiding feature 538 could be considered to be an extension or indication of the position of the landmark, as well. The hexagonal edges of the centrally located instrument guiding feature 538 may also be helpful in interacting with the hexagonal handling feature 426 of the instrument 316 to "grip" and transmit force (especially rotational force) between the guide 530 and the instrument in a way that the other, substantially cylindrical guiding features shown in FIG. 5 might not be able to accomplish.

As depicted in FIG. 6, the guide 530 may include a handling feature 426 which can be used with a handling tool (not shown) similarly to, and potentially in combination with, the handling features 426 of the instrument 316. Sometimes the available maneuvering space in a surgical field is relatively restricted, and it may be useful for a forceps, hex wrench (perhaps with a frictional fit or other feature to nest into the handling feature 426), Kocher tool, hemostat, or other user-manipulated handling tool (not shown) to selectively interact with the handling feature to hold the guide 520 or instrument 316 steady and/or to move the guide or instrument to a desired position. One or more features, such as indents, apertures, cavities, lugs, undercuts, or any other suitable structures could be provided to the handling feature 426 or to any other structure of the guide 530 or instrument 316 to facilitate gripping of the guide by any handling tool, in general, and/or by a particular handling tool.

Figure 7:
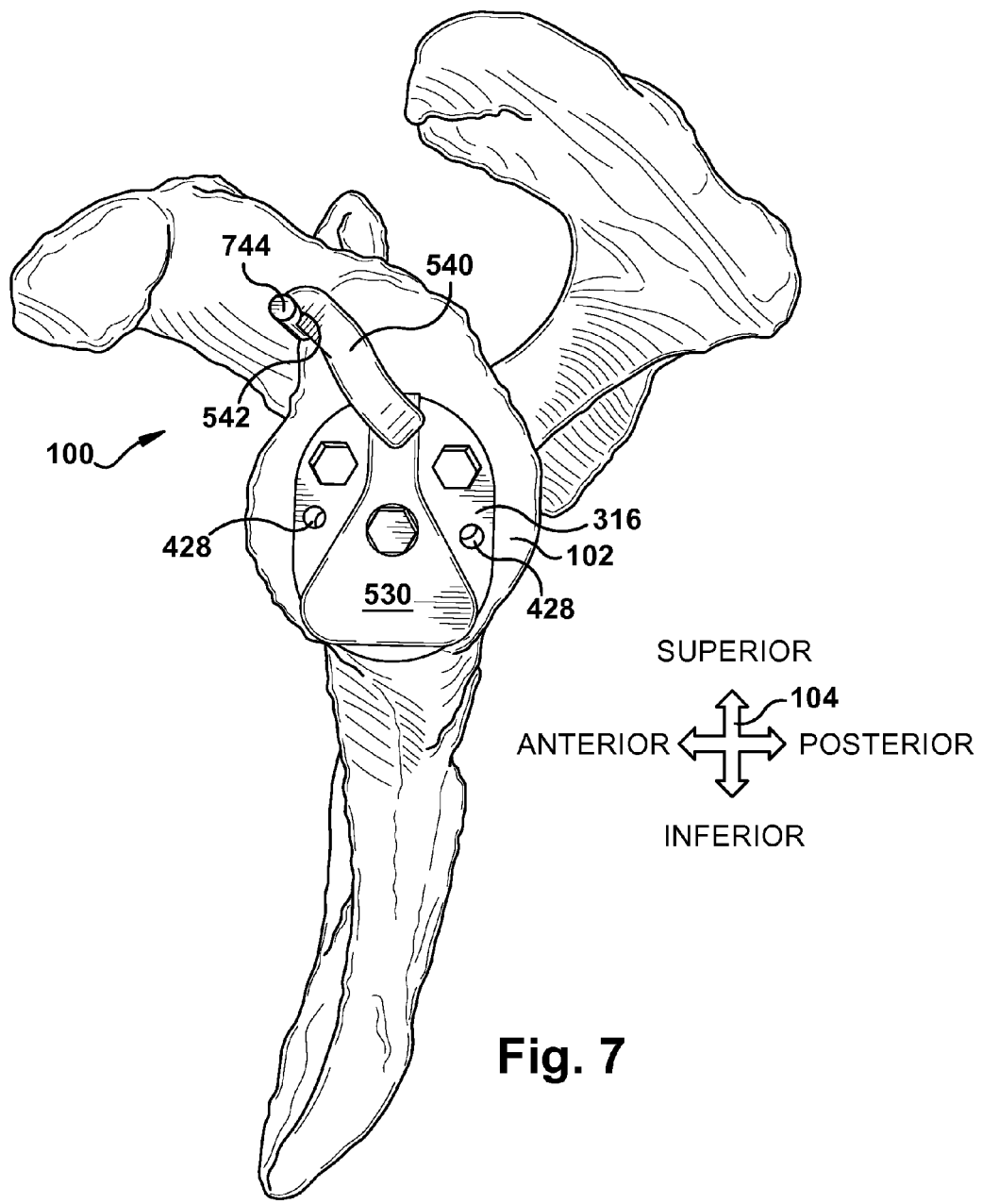
FIG. 7 is a top view of the embodiment of FIG. 5 and the instrument of FIG. 3 in the example use environment of FIG. 1.

An orienting feature 540, such as the depicted extension in FIGS. 5-7, may be provided to the guide 530. As shown here, for use with the instrument 316 in a glenoid implant 206 surgical procedure, the orienting feature 540 may extend, perhaps substantially, longitudinally and/or laterally from the guide 530, but the direction, amount, and type of extension will depend upon the location and type of body tissue with which the guide 530 is being used. The orienting feature 540 may be configured to enter a predetermined orienting relationship with a landmark (not shown), such as a guide pin, wire, marking, and/or other location indicator previously placed in a predetermined relationship with the patient tissue, such predetermined orienting relationship occurring when the lower guide surface 532 is in mating contact with at least a portion of the upper instrument surface 322 in a predetermined relative guide/instrument orientation. The achievement of the predetermined orienting relationship indicates that the instrument 316 has achieved a predetermined instrument relationship with the patient tissue. (The predetermined relative guide/instrument orientation is achieved when the guide 530 and instrument 316 are mated in a desired manner, as predetermined via preoperative imaging and/or analysis.)

The landmark for use with the orienting feature 540, similarly to any landmark used to help locate the shaft aperture as described above, may be any suitable two- or three-dimensional landmark and placed in any desired manner. It may be helpful for the landmark for use with the orienting feature 540 to be affixed to the patient tissue at a location spaced from a location of the stock instrument 530.

Optionally, the orienting feature 540 may include an orienting indicator 542. When present, the orienting indicator 542 may be configured to achieve a predetermined signaling relationship (the signaling relationship being directly related to the orienting relationship) with the landmark, as will be described below, while the guide 530 and the instrument 316 are in the predetermined relative guide/instrument orientation. For example, in the first embodiment shown in FIGS. 5-7, the orienting feature 540 is a arm-type structure extending from the guide body 536 and the orienting indicator 542 is a notch in the orienting feature 540 shaped to somewhat closely surround at least a portion of the diameter of a guide pin or other three-dimensional landmark to achieve the predetermined signaling relationship. The landmark(s) were previously placed in any suitable manner in predetermined locations at the surgical site. Accordingly, the predetermined signaling relationship between the landmark(s) and the orienting indicator(s) 542 assists the user in placing the guide 530 into a predetermined guide orientation with respect to the patient tissue.

When the guide 530 and the instrument 316 are held in a predetermined relative guide/instrument orientation (e.g., through the use of the guide interacting feature 324 and instrument guiding feature 538, frictional engagement between the upper instrument surface 322 and lower guide surface 532, any other mechanical linkage, or even merely coordinated movement of each by the user), then the instrument is manipulated in concert with the guide. Accordingly, movement of the guide 530 into the predetermined guide orientation—as signaled by coordination of the landmark(s) and the orienting feature 540—will concurrently move the instrument 316 into a predetermined instrument orientation with respect to the patient tissue. One of ordinary skill in the art can readily preoperatively plan the placement and type of landmark(s), as well as the structure and type of orienting feature(s) 540 and/or orienting indicator(s) 542 to assist the user in guiding the instrument 316 into the predetermined instrument orientation and/or location with respect to the patient tissue for a particular application of the present invention.

While the orienting indicator 542 is shown in FIGS. 5-7 as being a notch, any suitable structure, notch-like or otherwise, could be used as an orienting indicator. For example, the orienting indicator 542 could be a lug extending from the orienting feature 540, a visual indicator such as a line drawn or etched on the orienting protrusion, or even a mechanical system such as a latch or trip-wire.

Much of the success of a prosthetic joint replacement arises from secure affixation of the glenoid implant 206 to the scapula 100, and anchoring of the fastening pegs 214 into robust bony matter contributes to a suitably snug fit between the glenoid implant and the scapula. However, pathological anatomy of the scapula 100 may affect where the fastening pegs 214 can be securely placed. The native and pathological anatomies differ from patient to patient, so preoperative patient imaging scans may be used to preoperatively plan desired locations and trajectories for the fastening pegs 214 to be inserted into the scapula 100. However, and particularly during minimally invasive surgeries, very little of the scapula 100 may be visible to the user, and the visible portion of the scapula may be located at the distal end of a "tunnel" of surrounding soft tissue temporarily retracted by the user—accordingly, available maneuvering space at the surgical site may be severely restricted. In addition, the patient's shoulder may be actually canted slightly differently during the surgical procedure than planned preoperatively. These are among the factors which may result in a preoperative plan for a particular glenoid implant 206 installation being very difficult and time-consuming for a user to actually perform in an operative environment.

To aid with carrying out a preoperative plan for attaching a stock prosthetic implant to a patient tissue, the guide 530 may be preoperatively generated. The guide 530 is at least partially custom-manufactured for a particular patient responsive to preoperative imaging of the patient tissue. For example, the guide 530 may be wholly custom-made (e.g., using rapid prototyping techniques) or may be modified from a stock guide or guide blank (not shown). It is contemplated that at least a part of the guide 530 is a patient-specific, single-use, bespoke feature suited only for use at the indicated surgical site. For example, a stock guide body 536 (e.g., the y-shaped portion of the structure in FIGS. 5-6) could be supplemented with a patient-specific orienting feature 540 (e.g., the protruding, asymmetrical arm structure in FIGS. 5-6). One of ordinary skill in the art could create a guide which uses a patient-specific "disposable" structure connected to a stock, generic "reusable" carrier in this manner, with any desired attachment mechanism connecting the two in a sufficiently rigid portion to carry out the interactions discussed herein.

Regardless of the whole/partial custom manufacture status, the guide 530 may be configured responsive to at least one of preoperative imaging of the patient tissue and preoperative selection of the stock prosthetic implant. Because the instruments 316 are stock items, related to specific stock prosthetic implants (e.g., the depicted glenoid implants 206), the guide 530 also may be at least partially a stock item. The orientation of the instrument 316 upon the glenoid fossa 102 is predetermined by a user before the guide 530 is provided. This predetermination may occur intraoperatively, as the user is able to directly see the condition of the surgical site. However, it is contemplated that a predetermination of the desired instrument orientation could be accomplished preoperatively, with reference to preoperative imaging of the patient tissue. In this manner, a user can create a patient tissue model for observation, manipulation, rehearsal, or any other pre-operative tasks.

The term "model" is used herein to indicate a replica or copy of a physical item, at any relative scale and represented in any medium, physical or virtual. The patient tissue model may be a total or partial model of a subject patient tissue, and may be created in any suitable manner. For example, and as presumed in the below description, the patient tissue model may be based upon computer tomography ("CT") data imported into a computer aided drafting ("CAD") system. Additionally or alternatively, the patient tissue model may be based upon digital or analog radiography, magnetic resonance imaging, or any other suitable imaging means. The patient tissue model will generally be displayed for the user to review and manipulate preoperatively, such as through the use of a computer or other graphical workstation interface.

During preoperative planning, the user can view the patient tissue model and, based upon knowledge of other patient characteristics (such as, but not limited to, height, weight, age, and activity level), then choose a desired stock prosthetic implant. Because three-dimensional image models are available of many stock prosthetic implants, the user may be able to "install" the stock prosthetic implant virtually in the patient tissue model via a preoperative computer simulation. During such a simulation, the user can adjust the position of the stock prosthetic implant with respect to the patient tissue, even to the extent of simulating the dynamic interaction between the two, to refine the selection, placement, and orientation of the stock prosthetic implant for a desired patient outcome. For example, a system similar to that of co-pending U.S. patent application Ser. No. 13/282,550, filed Oct. 26, 2011, titled "System of Preoperative Planning and Provision of Patient-Specific Surgical Aids" and claiming priority to U.S. Provisional Patent Application No. 61/408,392, filed Oct. 29, 2010 and titled "System of Preoperative Planning and Provision of Patient-Specific Surgical Aids", the entire contents of both of which are incorporated herein by reference, or any suitable preoperative planning system could be used.

Once a chosen stock prosthetic implant has been virtually placed in a desired position and orientation with respect to the patient tissue, the orientation of the implant, and thus of the instrument 316, can also be planned through the use of the computer simulation, with consideration of the location, amount, and pathology of the patient tissue being taken into account in instrument selection and placement planning. By hand and/or with automatic computer assistance, the user can experiment with various sizes, placements, and orientations for an instrument that can be used to help achieve the desired patient tissue remodeling. For example, the selected instrument 316 may contain at least one patient tissue modification feature (e.g., a reaming window, drill guide aperture, or any other structure which can help a user in placing and/or conducting some patient tissue modification), which indicates a predetermined location for a patient tissue modification procedure when the instrument is in the predetermined instrument orientation with respect to the patient tissue. In this manner, the final desired location of the fastening pegs 214 in the patient tissue, or any other patient tissue modification desired, may be used to work backward and determine selection of a suitable instrument 316 and from there to a predetermined instrument orientation on the glenoid fossa 102, both in terms of lateral positioning and rotational orientation.

When the instrument 316 positioning and selection has been finalized in a virtual manner, the guide 530 can be generated, and landmark(s) for interaction with the orienting feature 540 virtually placed with respect to the virtual instrument and the virtual patient tissue. The user may then have the opportunity to adjust the virtual guide 530 before a physical guide 530 is produced. (Hereafter, in the description of the first embodiment, the guide 530 is presumed to be physical.)

In FIG. 7, a scapula 100 is shown in an intraoperative arrangement. Here, the instrument 316 has been placed atop the glenoid fossa 102 with the instrument shaft 318 received into a shaft aperture. A landmark 744 has been placed at a predetermined landmark location chosen responsive to preoperative imaging of the patient tissue. Here, the landmark 744 is spaced from a location of the instrument 316.

The lower guide surface 532 of the guide 530 has been mated with a portion of the upper instrument surface 322 of the instrument 316 to place the instrument and guide into the predetermined relative guide/instrument orientation. The guide 530 and instrument 316 have then been concurrently moved (either both directly or by virtue of the interaction between some structure of the guide and a contacting structure of the instrument) to place the guide in the predetermined guide orientation with respect to the patient tissue, which means, since the guide and instrument are mated, that the instrument has achieved the predetermined instrument orientation with respect to the patient tissue. The user knows that the predetermined guide and instrument orientations have been achieved because the mated guide 530 and instrument 316 have been repositioned (here, rotated about the instrument shaft 318 pivotally held in the shaft aperture) to bring the orienting feature 540 into the predetermined orienting relationship with the landmark 744. More specifically in the depicted example of the Figures, since the orienting indicator 542 is a notch, the instrument 316 and mated guide 530 have been repositioned such that the landmark 744 is received into the orienting indicator 542. As an alternative to this agnostic placement of the guide 426 and nested/attached stock prosthetic implant at the surgical site and subsequent rotation into position, the guide 530 and the instrument 316 could be concurrently placed into contact with at least one landmark (which could include the central landmark) at a location spaced apart from the patient tissue at the surgical site. For example, a landmark could be an elongate guide pin (such as that shown in FIG. 7), and a notchlike orienting indicator 542 could be placed into the signaling relationship with a protruding end of the guide pin some distance from the patient tissue. In this optional situation, the stock instrument would be guided into the predetermined instrument orientation concurrently with being brought into contact with the patient tissue as the orienting indicator 542 slides along the length of the guide pin via a rail-like dynamic guiding technique.

Regardless of how the goal of placing the instrument 316 into the predetermined instrument orientation with respect to the patient tissue (glenoid fossa 102, here) is accomplished, the user may remove the guide 530, and optionally the landmark 744, from the surgical site and continue with the surgical procedure using the positioned instrument as desired once the predetermined instrument orientation has been achieved as shown in FIG. 7.

Optionally, the instrument 316 may be temporarily secured in the predetermined instrument orientation to avoid shifting or movement of the instrument upon the patient tissue. For example, guide pins (not shown) could be inserted through the securing features 428 to hold the instrument 316 in place for as long as desired by the user. Whether an additional structure is provided or the user merely holds the instrument 316 in place by hand, however, the desired patient tissue modifications are made, the instrument 316 is removed from the patient tissue, and the surgical procedure proceeds apace. This may include the insertion of one or more surgical tools through at least one guide interacting structure 324 of the instrument 316, since some of the guide interacting structures additionally function as drill guides for preparation of the patient tissue to receive the fastening pegs 214 of the glenoid implant 206 here.

FIGS. 8-12 depict a guide 530' according to a second embodiment of the present invention and related structures. The guide 530' of FIGS. 8-12 is similar to the guide 530 of FIGS. 5-7 and therefore, structures of FIGS. 8-12 that are the same as or similar to those described with reference to FIGS. 1-7 have the same reference numbers with the addition of a "prime" mark. Description of common elements and operation similar to those in the previously described first embodiment will not be repeated with respect to the second embodiment.

Figure 8:
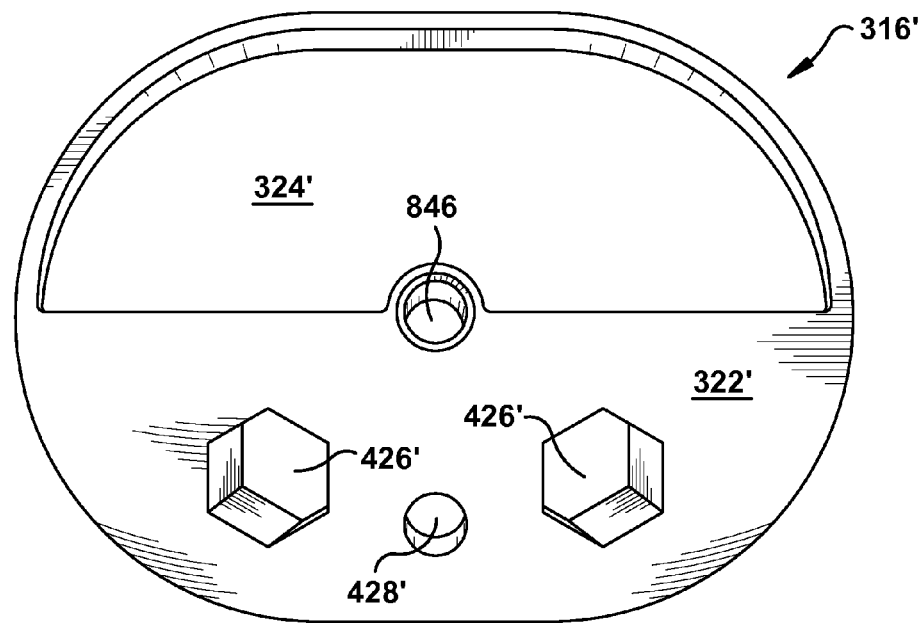
FIG. 8 is a top view of a second prior art instrument for use with the component of FIG. 2 or a similar component.
Figure 9:
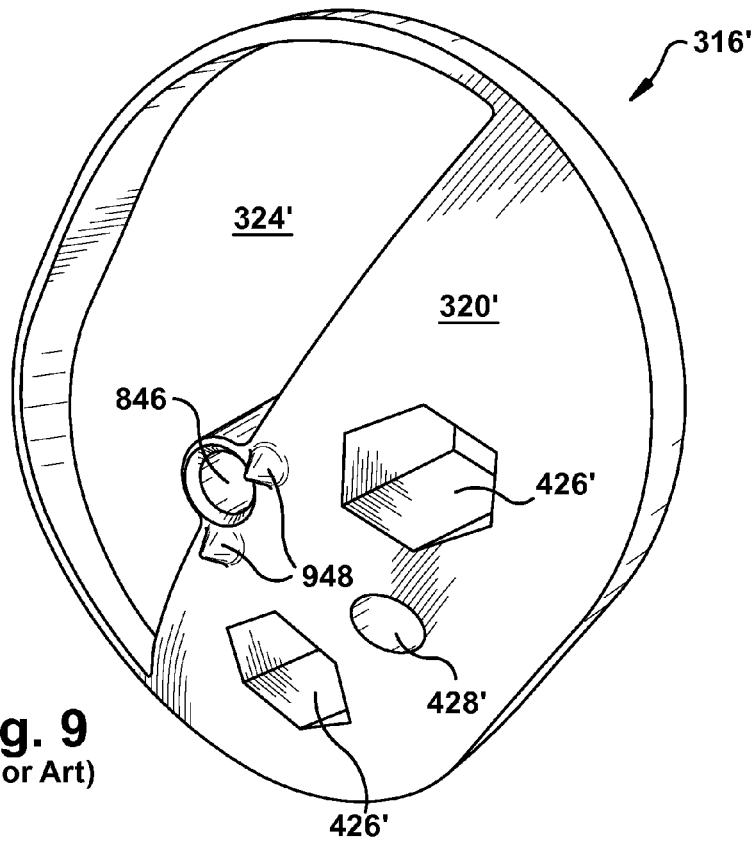
FIG. 9 is a perspective bottom view of the instrument of FIG. 8.

FIGS. 8-9 depict an instrument 316' which can be used to guide reaming or other relatively large-area patient tissue modification (as opposed to the relatively confined fastening peg 214 drilling guided by the first embodiment). To that end, the instrument 316' includes a relatively large guide interacting feature 324'. For example, the instrument 316' of FIG. 8 could be used with the glenoid implant 206 of FIG. 2 or with any other suitable glenoid implant (e.g., a known type of implant having a stepped lower implant surface, for which an area of the glenoid fossa 102' will need to be reamed away).

Additionally, the instrument 316' of the second embodiment does not have an instrument shaft 318, but instead has a locating aperture 846 which accepts a three-dimensional landmark (not shown) to position the instrument 316' laterally upon the glenoid fossa 102 as desired. The landmark which enters the locating aperture 846 could be a guidewire (not shown), such as that disclosed in co-pending U.S. patent application Ser. No. 13/178,324, filed Jul. 7, 2011, titled "Method and Apparatus for Providing a Relative Location Indication During a Surgical Procedure" and claiming priority to U.S. Provisional Patent Application Ser. No. 61/362,722, filed Jul. 9, 2010, and titled "Method and Apparatus for Providing a Relative Location Indication During a Surgical Procedure", the contents of both of which are hereby incorporated by reference in their entirety. The landmark (not shown) received by the locating aperture 846 may have been previously placed to provide a "pivot point" about which the instrument 316' can rotate during guided movement as discussed below. This landmarking/pivot-guiding function is provided instead by indirect action of the instrument shaft 318 in the first embodiment of the present invention, as previously discussed.

The lower instrument surface 320' of the instrument 316' of the second embodiment also includes a plurality of holding teeth 948 which can be selectively pushed down into the patient tissue to resist rotation/pivoting of the instrument about the landmark within the locating aperture 846.

Figure 10:
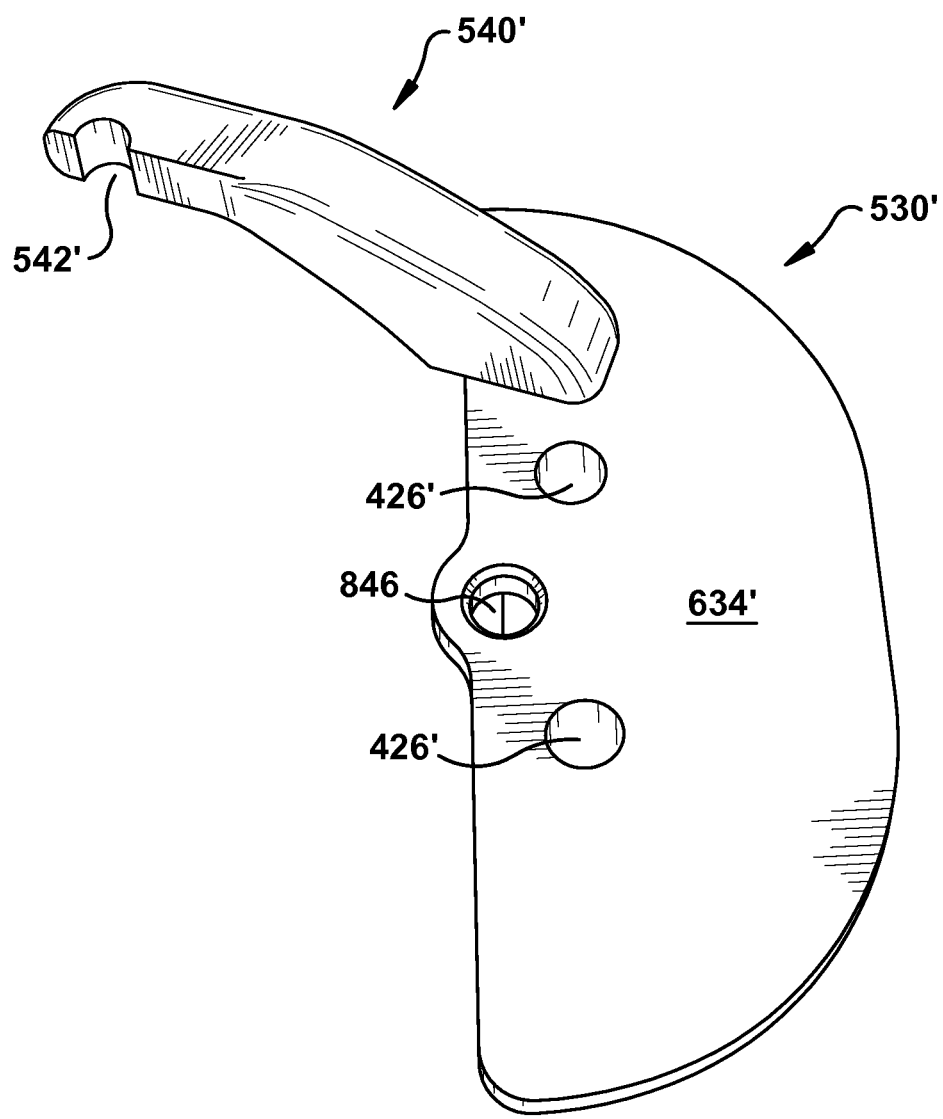
FIG. 10 is a top view of an embodiment of the present invention.
Figure 11:
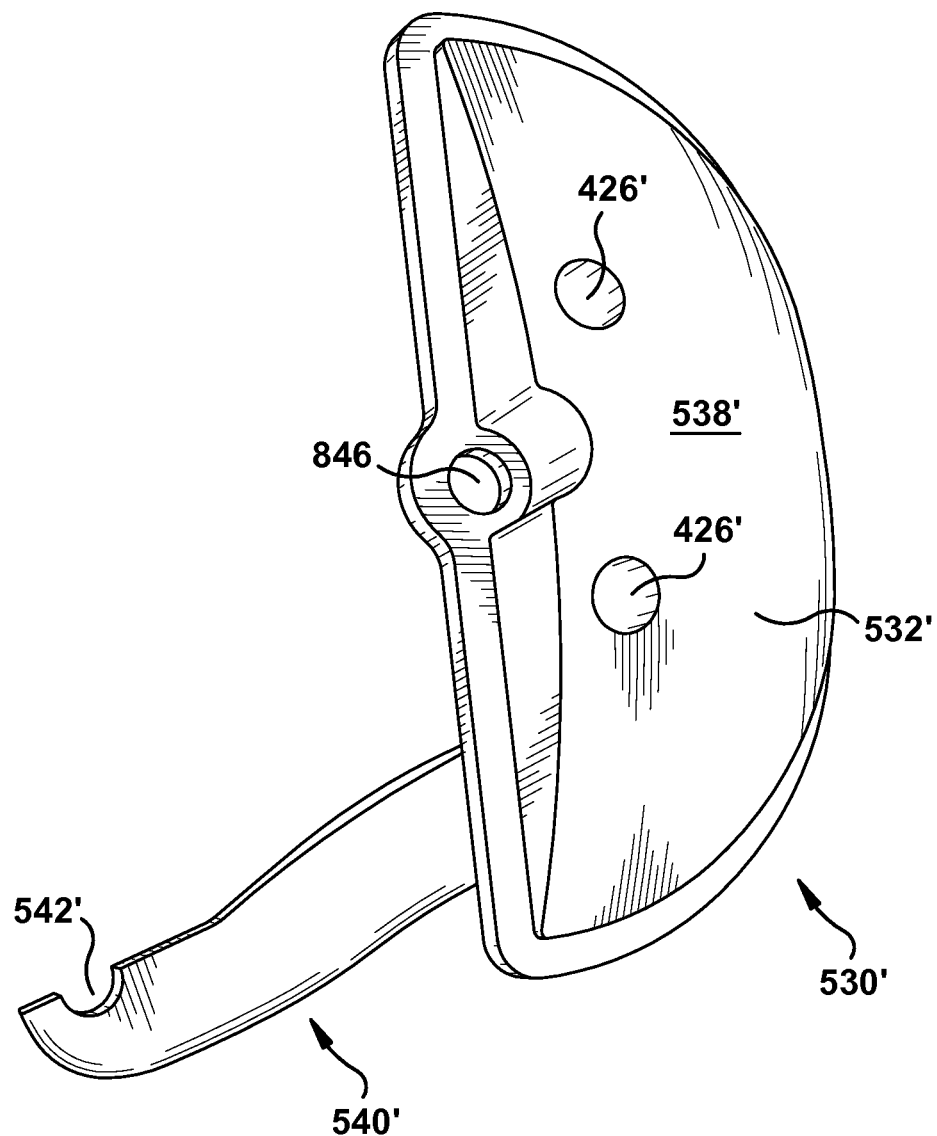
FIG. 11 is a bottom view of the embodiment of FIG. 10.

A guide 530' according to the second embodiment of the present invention is shown in FIGS. 10-11. Like the instrument 316', the guide 530' includes a locating aperture 846. The guide 530' may include one or more handling features 426' (two shown), which may be configured to accept a handling tool (not shown) or otherwise to assist the user in moving the guide at or near the surgical site.

Figure 12:
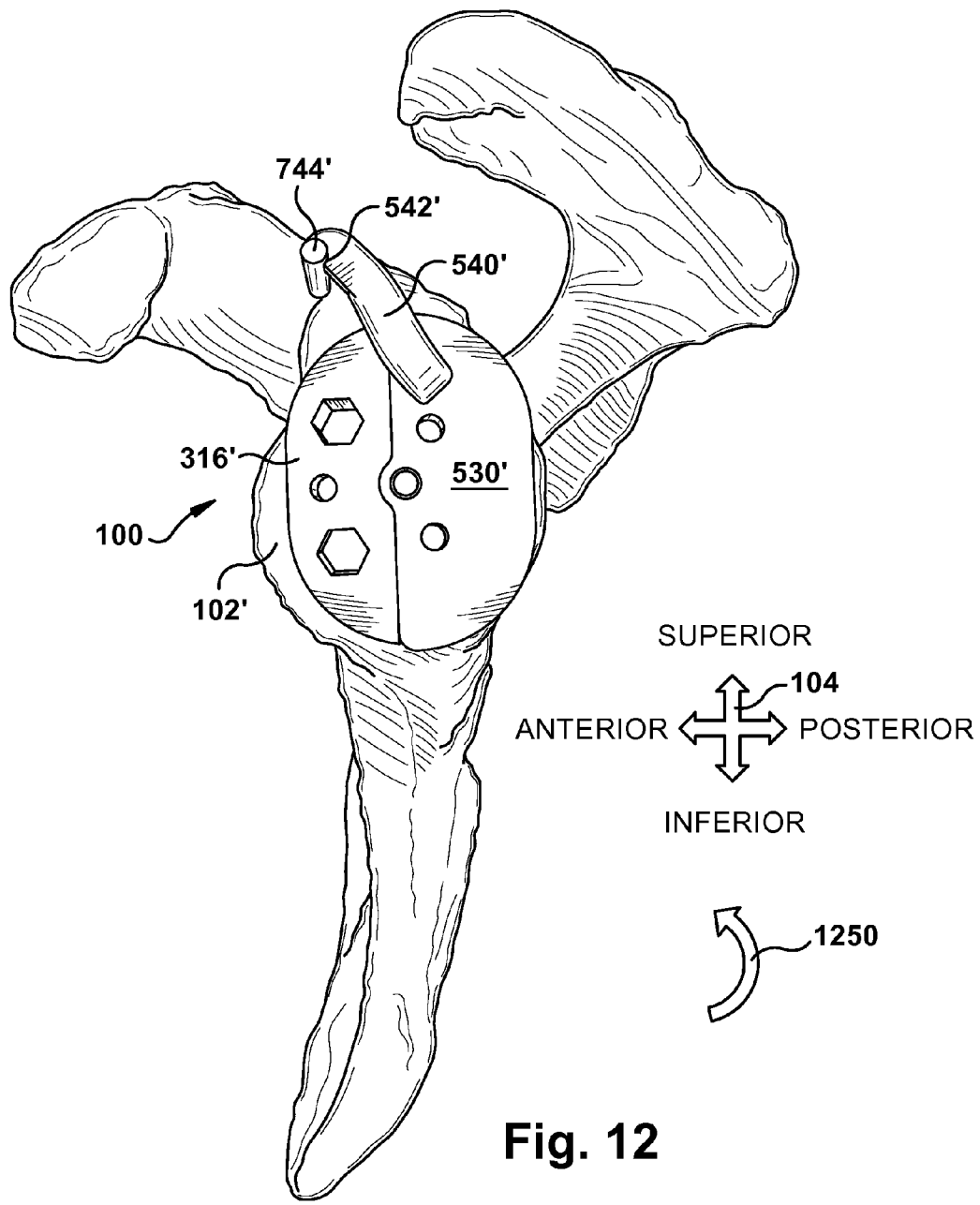
FIG. 12 is a top view of the embodiment of FIG. 10 and the instrument of FIG. 8 in the example use environment of FIG. 1.

In use, the guide 530' of the second embodiment operates similarly to the guide 530 of the first embodiment, as is shown in FIG. 12. The instrument 316' of FIGS. 10-11 is placed upon the glenoid fossa 102 surface. Optionally, a landmark (not shown) may have been previously placed in the glenoid fossa 102 surface—if so, the locating aperture 846 receives the landmark as a part of placing the lower instrument surface 320' in contact with the patient tissue. The guide 530' is placed atop the instrument 316' with the lower guide surface 532' in contact with the upper instrument surface 322'. When present, the instrument guiding features 538' of the guide 530' may mate with the guide interacting features 324' of the instrument 316'.

Once the instrument 316' and guide 530' are mated together in the predetermined relative guide/instrument orientation atop the glenoid fossa 102' surface, the instrument and guide can be moved concurrently to move both the guide and the instrument into predetermined guide and instrument orientations with respect to the patient tissue. In other words, engagement between the guide 530' and the instrument 316' causes forces exerted upon the guide to be transferred to the instrument, and the user can move both the instrument and the guide concurrently either by moving just the guide, or by moving both the guide and instrument directly. For example, and presuming that the instrument 316' includes a locating aperture 846 which accepts a landmark (not shown) placed in the glenoid fossa 102' surface, a counterclockwise force (indicated by counterclockwise arrow 1250 in FIG. 12) exerted upon the orienting feature 540' will pivot the guide 530"—and thus the mated instrument—about the landmark.

The guide 530' and mated instrument 316' may be rotated, for example, until the orienting indicator 542' achieves a predetermined signaling relationship with a landmark 744' such as the depicted guide pin. Accordingly, the guide 530' can rotate the instrument 316' into a predetermined instrument orientation with respect to the glenoid fossa 102' surface.

When at least one landmark 744' (when present) is a guide pin or other elongate three-dimensional structure, the guide pin may deflect, if needed, to allow the guide 530' to be lifted longitudinally off the protruding end guide pin. The guide 530' may include at least one frangible portion to allow substantially laterally-oriented removal of the guide from around the guide pin or from engagement with the instrument 316'. As another option, the guide 530' could include one or more slots (not shown) to allow removal of the guide by sliding the guide sideways away from the guide pin and/or the instrument 316'. The above description presumes that the guide 530 and instrument 316 are removed from the patient tissue before completion of the surgery. It is contemplated, nevertheless, that the guide and/or a stock instrument component could be configured for maintenance of the guide and/or instrument within the body, perhaps as a part of the completely installed prosthetic implant structure.

It is also contemplated that the guide 530 may be used in conjunction with an implant and related structures such as those discussed in co-pending U.S. patent application Ser. No. 13/282,495, filed Oct. 27, 2011, titled "System and Method for Assisting with Attachment of a Stock Implant to a Patient Tissue" and claiming priority to U.S. Provisional Patent Application No. 61/408,324, filed Oct. 29, 2010 and titled "System and Method for Assisting with Attachment of a Stock Implant to a Patient Tissue", the entire contents of both of which are incorporated herein by reference.

While aspects of the present invention have been particularly shown and described with reference to the preferred embodiment above, it will be understood by those of ordinary skill in the art that various additional embodiments may be contemplated without departing from the spirit and scope of the present invention. For example, the specific methods described above for using the guide 530 are merely illustrative; one of ordinary skill in the art could readily determine any number of tools, sequences of steps, or other means/options for placing the above-described apparatus, or components thereof, into positions substantially similar to those shown and described herein. Any of the described structures and components could be integrally formed as a single piece or made up of separate sub-components, with either of these formations involving any suitable stock or bespoke components and/or any suitable material or combinations of materials; however, the chosen material(s) should be biocompatible for most applications of the present invention. The mating relationships formed between the described structures need not keep the entirety of each of the "mating" surfaces in direct contact with each other but could include spacers or holdaways for partial direct contact, a liner or other intermediate member for indirect contact, or could even be approximated with intervening space remaining therebetween and no contact. Though certain components described herein are shown as having specific geometric shapes, all structures of the present invention may have any suitable shapes, sizes, configurations, relative relationships, cross-sectional areas, or any other physical characteristics as desirable for a particular application of the present invention. An adhesive (such as, but not limited to, bone cement) could be used in conjunction with the system and method described herein. The guide 530 may include a plurality of structures cooperatively forming the base body and temporarily or permanently attached together in such a manner as to permit relative motion (e.g., pivoting, sliding, or any other motion) therebetween. Any structures or features described with reference to one embodiment or configuration of the present invention could be provided, singly or in combination with other structures or features, to any other embodiment or configuration, as it would be impractical to describe each of the embodiments and configurations discussed herein as having all of the options discussed with respect to all of the other embodiments and configurations. An adhesive (such as, but not limited to, bone cement) could be used in conjunction with the system and method described herein. Any of the components described herein could have a surface treatment (e.g., texturization, notching, etc.), material choice, and/or other characteristic chosen to provide the component with a desired interaction property (e.g., tissue ingrowth, eluting of a therapeutic material, etc.) with the surrounding tissue. A device or method incorporating any of these features should be understood to fall under the scope of the present invention as determined based upon the claims below and any equivalents thereof.

Other aspects, objects, and advantages of the present invention can be obtained from a study of the drawings, the disclosure, and the appended claims.

Having described the invention, we claim:

1. A method of arranging a stock instrument with respect to a patient tissue, the stock instrument including at least one guide interacting feature, the method comprising the steps of:
   affixing a landmark to the patient tissue at a predetermined first landmark location;
   placing a lower instrument surface of the stock instrument into contact with the patient tissue at a second location spaced apart from the predetermined first landmark location;
   providing a guide having a lower guide surface contoured to mate with at least a portion of an upper instrument surface of the stock instrument, the upper and lower instrument surfaces being opposite surfaces of the stock instrument, an upper guide surface spaced longitudinally apart from the lower guide surface by a guide body, the guide also having at least one instrument guiding feature at a predetermined feature location with respect to the guide body and an orienting feature, the orienting feature comprising an arm extending from the upper guide surface, and the arm having a corresponding landmark engaging portion;
   defining a predetermined orientation of the stock instrument on the patient tissue, the predetermined orientation being preselected responsive to preoperative imaging of the patient tissue;
   placing the lower guide surface into mating contact with at least a portion of the upper instrument surface wherein the at least one guide interacting feature of the stock instrument is placed into engagement with the at least one instrument guiding feature of the guide, such that the guide and the stock instrument are engaged in fixed relative orientation and displaceable together as a guide assembly; and
   moving the stock instrument into the predetermined orientation on the patient tissue by moving the guide assembly, while the lower instrument surface of the stock instrument remains in contact with the patient tissue at the second location, until the corresponding landmark engaging portion of the arm of the orienting feature abuts against the landmark affixed to the patient tissue, thereby immobilizing the guide assembly relative to the patient tissue at the predetermined orientation.

2. The method of claim 1, including a step of securing the stock instrument in the predetermined orientation with respect to the patient tissue before removing the guide from engagement with the instrument.

3. The method of claim 2, wherein the step of securing the stock instrument in the predetermined orientation includes the step of placing at least one guide pin through a corresponding securing feature in the stock instrument.

4. The method of claim 1, wherein the step of moving the guide includes the steps of:
providing an orienting indicator to the orienting feature; and
repositioning the guide to bring the orienting indicator into a predetermined signaling relationship with the landmark.

5. The method of claim 1, wherein a chosen one of the at least one guide interacting feature and the at least one instrument guiding feature is a protrusion and the other one of the at least one guide interacting feature and the at least one instrument guiding feature is a cavity, and the protrusion enters the cavity to engage the guide and the stock instrument in the mating contact.

6. The method of claim 1, wherein the step of providing the guide includes at least one of the steps of:
custom-manufacturing the guide responsive to at least one of preoperative imaging of the patient tissue and preoperative selection of the stock instrument; and
modifying a stock guide responsive to at least one of preoperative imaging of the patient tissue and preoperative selection of the stock instrument.

7. The method of claim 6, wherein the step of modifying the stock guide includes the step of providing a custom-manufactured orienting feature to the stock guide.

8. The method of claim 1, wherein the predetermined first landmark location is chosen responsive to preoperative imaging of the patient tissue.

9. A method of arranging a stock instrument with respect to a patient tissue, the stock instrument including at least one guide interacting feature, the method comprising the steps of:
affixing at least one landmark to the patient tissue at a first landmark location;
placing a lower instrument surface of the stock instrument into contact with the patient tissue at a second location spaced apart from the first landmark location;
providing a guide having a lower guide surface contoured to mate with at least a portion of an upper instrument surface of the stock instrument, the upper and lower instrument surfaces being opposite surfaces of the stock instrument, an upper guide surface spaced longitudinally apart from the lower guide surface by a guide body, the guide having at least one instrument guiding feature at a predetermined feature location with respect to the guide body, the guide having an orienting feature, the orienting feature comprising an arm extending from the upper guide surface, the arm including a corresponding landmark engaging portion;
defining a predetermined orientation of the stock instrument on the patient tissue, the predetermined orientation being preselected responsive to preoperative imaging of the patient tissue;
placing the lower guide surface into mating contact with at least a portion of the upper instrument surface and engaging the guide and the stock instrument together to form a guide assembly wherein relative rotation between the guide and the stock instrument is prevented; and
moving the stock instrument into the predetermined orientation on the patient tissue by moving the guide assembly, while the lower instrument surface of the stock instrument remains in contact with the patient tissue at the second location, until the corresponding landmark engaging portion of the arm of the orienting feature abuts against the at least one landmark affixed to the patient tissue, thereby immobilizing the guide assembly relative to the patient tissue at the predetermined orientation.

10. The method of claim 9, wherein moving the guide assembly further comprises rotating the guide assembly to bring an orienting indicator of the orienting feature into a predetermined signaling relationship with the at least one landmark.

11. The method of claim 9, wherein the at least one landmark includes a pin and the corresponding landmark engaging portion includes a corresponding notch formed in the arm of the orienting feature.

12. The method as defined in claim 9, wherein engaging the guide and the stock instrument together further comprises placing the at least one instrument guiding feature of the guide into engagement with at least one guide interacting feature of the stock instrument.

13. The method of claim 12, wherein a chosen one of the at least one guide interacting feature and the at least one instrument guiding feature is a protrusion and the other one of the at least one guide interacting feature and the at least one instrument guiding feature is a cavity, and the protrusion enters the cavity to engage the guide and the instrument in the mating contact.

14. The method of claim 9, further comprising custom-manufacturing the guide responsive to at least one of preoperative imaging of the patient tissue and preoperative selection of the stock instrument, the guide thereby being patient-specific.

15. The method of claim 9, further comprising modifying a stock guide responsive to at least one of preoperative imaging of the patient tissue and preoperative selection of the stock instrument.

16. The method of claim 15, further comprising providing a custom-manufactured orienting feature to the stock guide.

17. The method of claim 9, wherein
the first landmark location is chosen responsive to preoperative imaging of the patient tissue.

* * * * *